Figure 1:
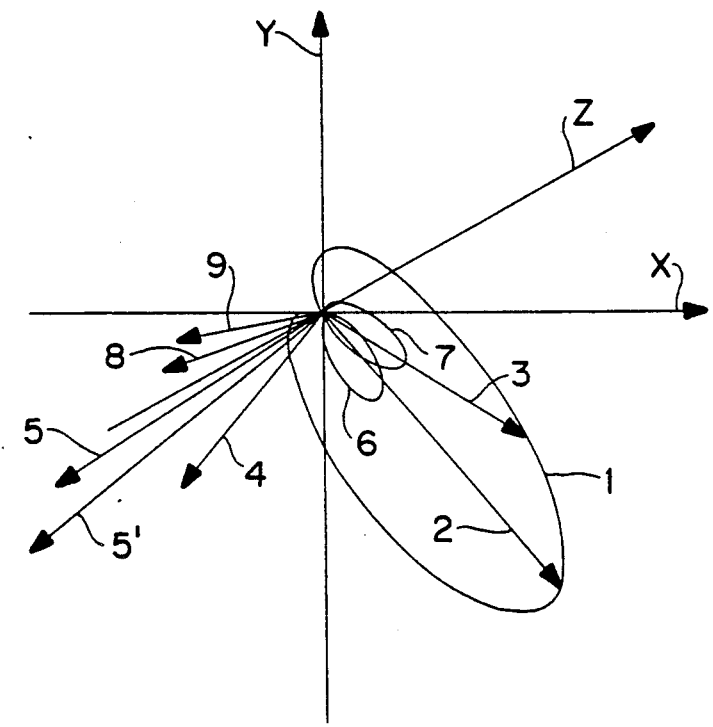

United States Patent [19]

Schmid

[11] Patent Number: 5,101,833

[45] Date of Patent: Apr. 7, 1992

[54] PROCESS FOR THE ACQUISITION OF MEASURED VALUES ON THE HUMAN AND ANIMAL BODY

[75] Inventor: Johann J. Schmid, Buchs, Switzerland

[73] Assignee: Studer Revox AG, Regensdorf, Switzerland

[21] Appl. No.: 642,785

[22] Filed: Jan. 18, 1991

[30] Foreign Application Priority Data

Jan. 22, 1990 [CH] Switzerland .................... 186/90

[51] Int. Cl.$^5$ ........................................ A61B 5/0402
[52] U.S. Cl. ..................................................... 128/699
[58] Field of Search ................... 128/699; 364/413.05

[56] References Cited

U.S. PATENT DOCUMENTS

| | | | |
|---|---|---|---|
| 3,548,813 | 12/1970 | Berner | 128/699 |
| 3,884,221 | 5/1975 | Eastman | 128/699 |
| 4,085,407 | 4/1978 | Stratbucker et al. | 128/699 |
| 4,121,576 | 10/1978 | Greensite | 128/699 |
| 4,136,690 | 1/1979 | Anderson et al. | 128/699 |
| 4,478,223 | 10/1984 | Allor | 128/699 |
| 4,569,357 | 2/1986 | Sanz et al. | 128/699 |
| 4,587,976 | 5/1966 | Schmid et al. | 129/699 |
| 4,700,712 | 10/1987 | Schmid | 128/699 |
| 4,922,920 | 5/1990 | Thie et al. | 128/699 |

FOREIGN PATENT DOCUMENTS 0278215 8/1988 European Pat. Off. .

*Primary Examiner*—William E. Kamm
*Assistant Examiner*—J. Jastrzab
*Attorney, Agent, or Firm*—Roylance, Abrams, Berdo & Goodman

[57] ABSTRACT

In order that in those processes in which vectors (2, 3) and vector loops (1) are determined from the measured values and which e.g. represent the heart function, is possible to better determine changes on loops brought about by changes in the heart, it is proposed that a vector product (4) should be determined from vectors determined at successive times and that the path of such vector products should be followed over a period.

6 Claims, 4 Drawing Sheets

PROCESS FOR THE ACQUISITION OF MEASURED VALUES ON THE HUMAN AND ANIMAL BODY

The invention relates to a process for the acquisition of measured values on the human and animal body, on the basis of electrical potentials, which are read off the body in such a way that a vector can be derived therefrom which represents an electrical field, which is produced by the heart and which generates the potentials.

Such processes are e.g. known from U.S. Pat. No. 4,569,357 and European patent application 278215. The U.S. patent shows how a vector can be derived from potentials, which result from the electrical field, which is produced by the heart of a human or animal. The European patent application shows that such vectors can be determined at random times and that further quantities can be determined from two such vectors, which are acquired at different times. For example these are differential vectors between two vectors or the surface covered by the vector per unit of time. This is intended to lead to the optimum detection of the shape of a loop, which is traversed by the tip of the vector with time.

The disadvantage of this process is that the abnormal changes which can occur in the heart do not necessarily have the consequence of a modified position or amount of a maximum vector. In addition, such abnormal changes do not always lead to corresponding changes in the shape of the loop or existing changes on the loop are sometimes not sufficiently clearly expressed in the known representation forms. This disadvantage could admittedly be obviated by three-dimensional representation of the loop as a result of much greater effort and expenditure, but additional information would be required e.g. concerning the speed of the vector at each point of the loop in order to establish the most important changes during and in the way in which the loop is traversed.

The invention, as characterized in the claims, solves the problem of providing a process for acquiring measured values, which obviates the aforementioned disadvantages and makes it possible with limited expenditure to detect the path of the loop of a vector and its divergences.

According to the invention this is achieved in that the vector, whose tip traverses a loop during time, is determined at different successive times and in that a vector product is formed from in each case two such vectors. Successively determined vector products are so graphically or numerically represented, that their time change can be established.

The advantages resulting from the invention are in particular that changes to the path or shape of loops determined at time intervals on the same human or animal, can be recognized better and more easily. In particular, changes during the production of the loops are recognized. As a result of the inventive process it is e.g. also possible to recognize whether specific areas of the loop are more rapidly or slowly tranversed by the vector at a different time. Due to the fact that changes on loops can be more easily and reliably detected, it is also possible to more accurately located ischemias. It is also easier to differentiate clearly between ischemia and other causes which modify the loops. Thus, better differentiation is made possible. The process according to the invention can also be more easily used with other supplementary methods in diagnostic systems.

The invention is described in greater detail hereinafter relative to the drawings, wherein show:

FIG. 1—Loops in space in a perspective view.

Figure 2:
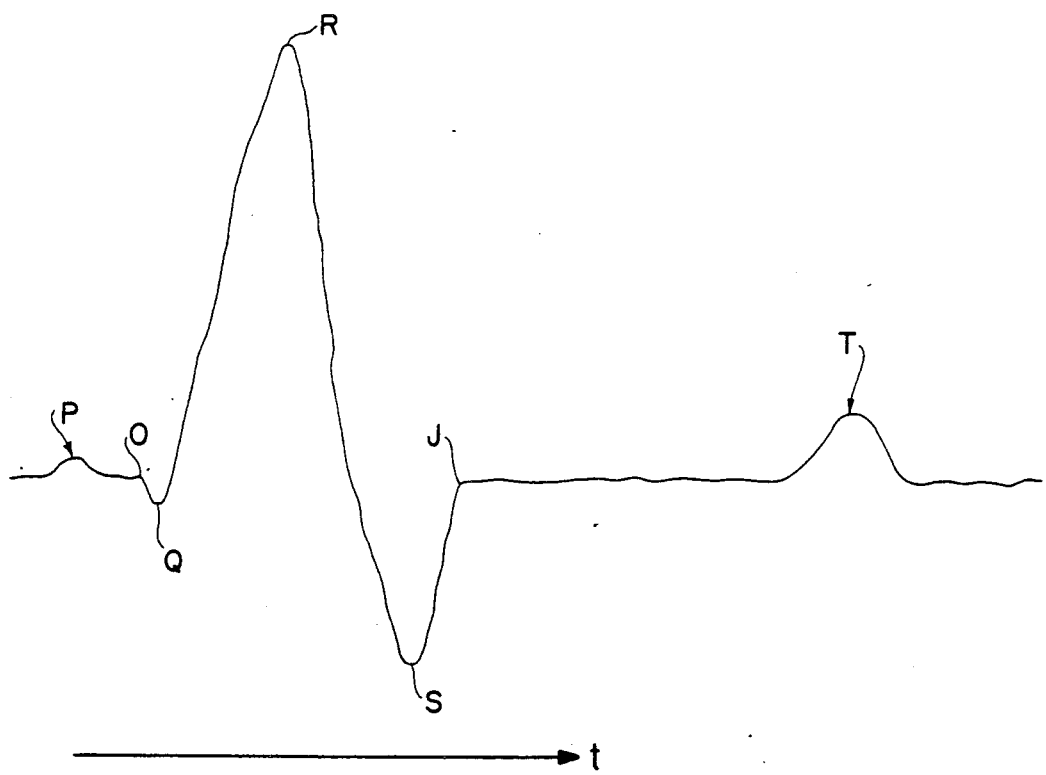

FIG. 2—The representation of an electrical potential as a function of time and in one dimension.

Figure 3:
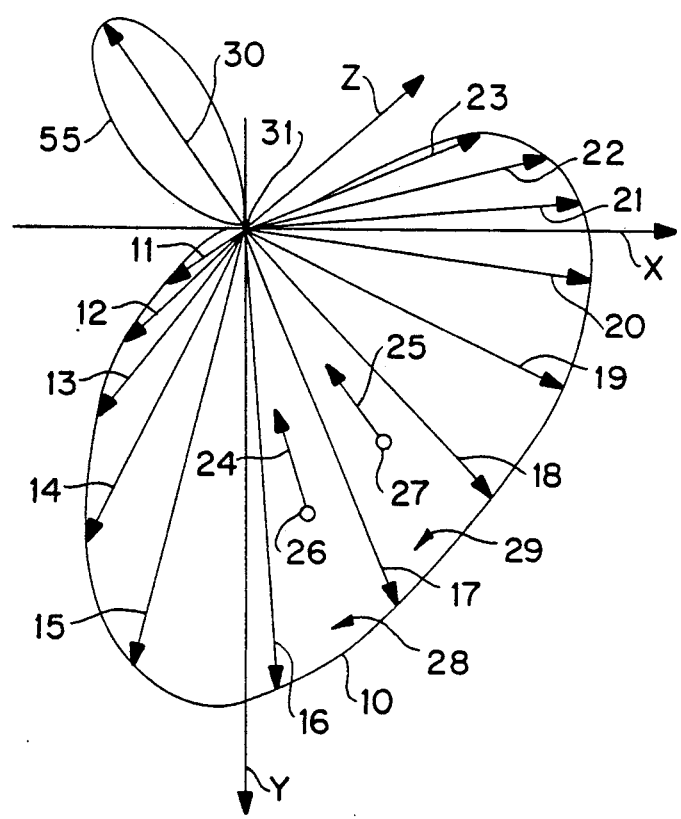

FIG. 3—A further loop according to FIG. 1, but on a larger scale.

Figure 4:
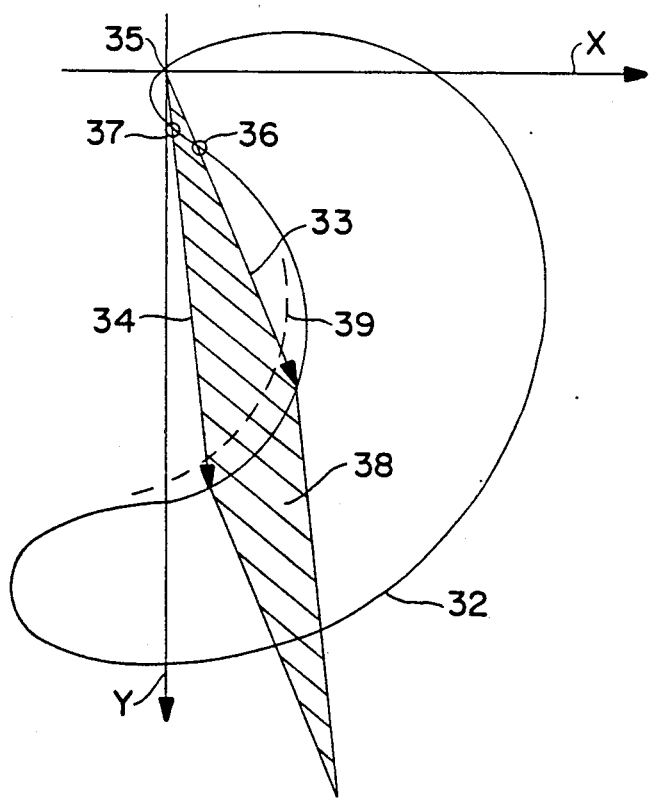

FIG. 4—A further loop as in FIG. 3 on a larger scale.

Figure 5:
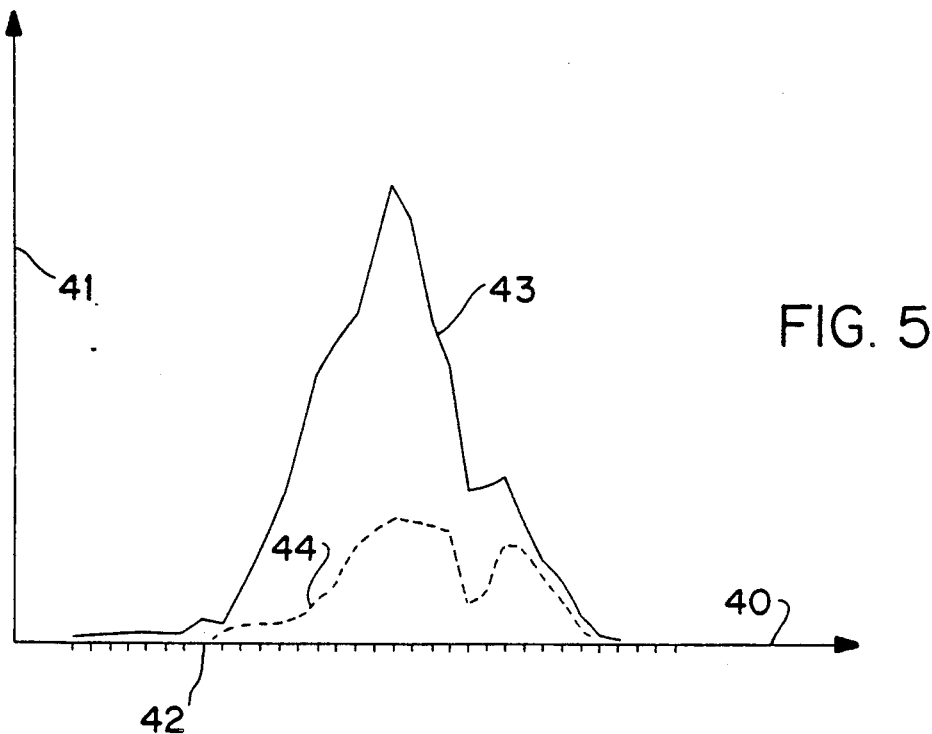

FIG. 5—A representation of the amounts of vector products.

Figure 6:
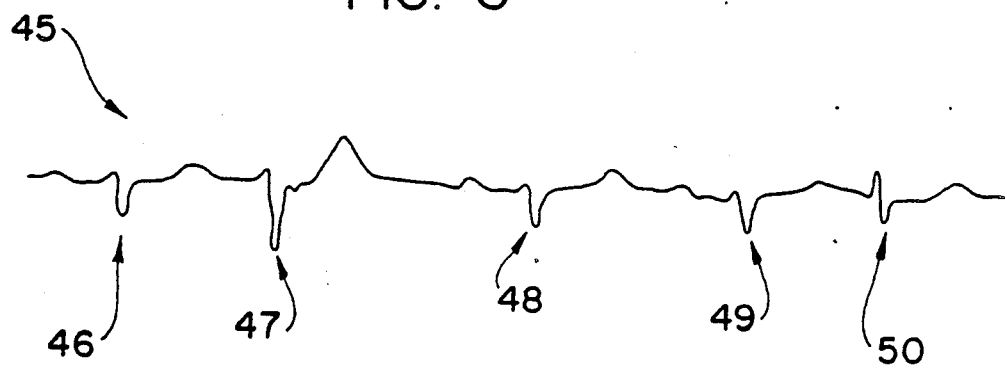

FIG. 6—A representation of signals of several heart beats.

Figure 7:
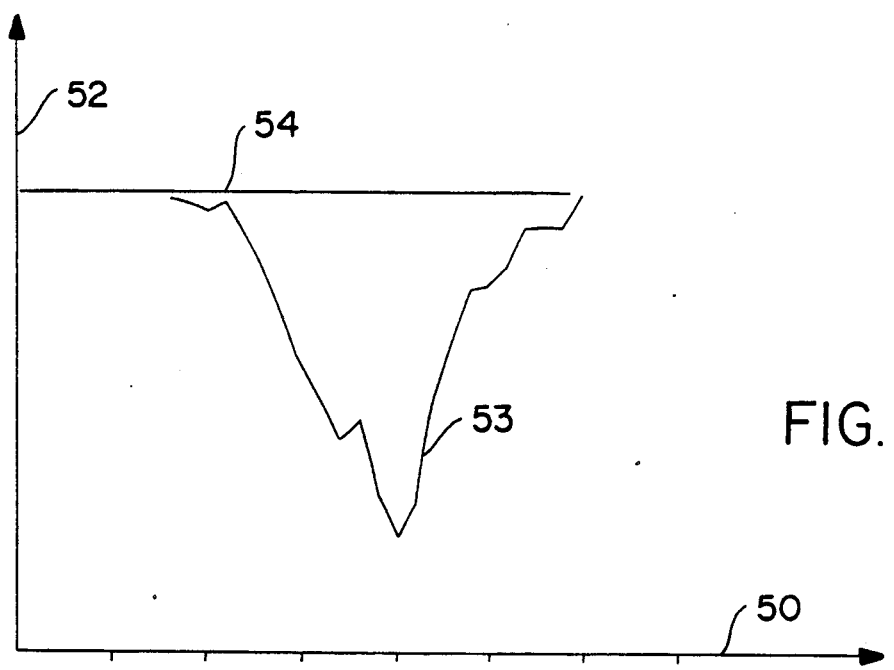

FIG. 7—A further special representation of vector products.

FIG. 1 shows a loop 1 as a geometrical locus of tips of vectors in space. The space is represented by a x-axis, a y-axis and a z-axis, which e.g. relate to a human or animal body. In the case of a human, the loop 1 represented in exemplified manner is also known as a QRS loop. It results from the position of the tip of a vector at different times, which represents an electrical field, which is produced by the heart. This vector is determined at times which are predetermined by a sequence of times, e.g. a scanning sequence. For the represented loop 1, the sequence has an infinite number of times, which have an infinite small reciprocal interval. In scanned systems the sequence has a finite number of times with a finite reciprocal interval. At a first time a vector 2 is determined and represented and at a second time a vector 3. A vector 4 represents a vector product, which is determined from the two vectors 2 and 3. The vector 4 is at right angles to the vectors 2 and 3 and can be calculated from the formula:

$$V(t+T-t) = (V(t) \times V(t+T))$$

in which $V(t+T-t)$ corresponds to the vector 4, i.e. the vector product, $V(t)$ to the vector 2 and $V(t+T)$ to the vector 3.

The vectors 2 and 3 are e.g. determined in the manner described in U.S. Pat. No. 4,569,357. In the case of vectorial addition of the vector products, a vector 5 represents the sum of the vector products calculated for the loop 1. However, the vector products can also be numerically added and then a further vector 5' is formed. An also shown loop 6 is also known as a T loop and a further loop 7 as a P loop. Vectors 8 and 9 are vectors, which are e.g. obtained by the vectorial addition of the vector products of the loops 6 and 7.

FIG. 2 plots electrical potentials or potential differences, or the values thereof, as a function of the time T. It is possible to see the characteristic points O, Q, R, S, I and the P and T waves which are known from the electrocardiography of the human heart. The aforementioned points can define the start and finish of different periods, e.g. repolarization, depolarization, QRS complex, etc.

FIG. 3 shows a further loop 10 in space and covers the tips of vectors 11 to 23 determined at the times of a given sequence of times. It is possible to determine from each pair of two vectors 11 12, 12 13, etc. vector products or, what amounts to the same, centroid vectors. Such centroid vectors 24 25 are shown in two cases and occur in the centroid 26, 27 of in each case one triangle 28, 29, which is formed by the vectors 16, 17 and 17, 18 and not shown differential vectors for the same. A sum of such centroid vectors forms a sum vector 30, which is displaced in a starting and final point 31 of the loop 10 in accordance with vector analysis rules. The vector, which is represented by the vectors 11 to 23 at different times, is formed by the loop 10, e.g. in the counterclockwise direction. Thus, it is possible to continuously form the vector products from the previously determined vectors. It is therefore also possible to continuously form the sum (numerically or vectorially added) of the vector products or the centroid vectors. Thus, the sum vector is obtained at different times, which is represented by a loop 55, which thus passes through the vector tip.

FIG. 4 shows a loop 32 with a special shape in space. The special shape is that the vectors 33 and 34, which in each case emanate from the starting and final point 35 of the loop 32, intersect the latter at points 36 and 37. The vector product of the vectors 33, 34 gives the surface of a parallelogram 38. It is clear that the surface of the loop 32 is not calculated by these vector products. Nevertheless it is appropriate to determine said vector products, because they give the desired information on the path of the loop 32, even in this special case. This is apparent on investigating how the vector product changes if the loop 32 changes at this point and would then have a path as represented by the line 39. As a result of a modified stressing of the heart, the loop 32 can have this other path. In this case the vectors 33, 34 would be smaller, as would the vector product.

In FIG. 5 vector product values are plotted over a horizontal time axis 40. These values can be read off the vertical axis 41, if a scale is applied to the latter. The vector products are determined at times of a sequence and such times are indicated by corresponding marks 42 on the time axis 40. On linking the individual values of the vector products, then a curve 43 is obtained, which shows the time change of successive vector products or their time sequence. The curve 43 corresponds to values of vector products, such as were e.g. determined on a human with an unstressed heart. A further curve 44 shows values of vector products as determined on the same human with a stressed heart.

FIG. 6 shows a signal 45 of the same type as in FIG. 2, but for several successive heart beats. This signal 45 inter alia comprises five QRS complexes 46, 47, 48, 49, 50, which do not all have comparable shapes and can be placed in three different classes. Complexes 46, 48 and 49 belong to a first class, complex 47 belongs to a second class and complex 50 to a third class. Therefore complexes 46, 48, 49 of the first class only have minor deflections and in particular almost no upward deflection. The complex 47 of the second class has the greatest deflections and the complex 50 of the third class has only small deflections, but they are roughly equal in the upwards and downwards directions. In this way, using corresponding predetermined threshold values, classes can be defined for the deflections.

Differential values between the values represented by the curves 43 and 44 are shown in FIG. 7 over axes 50, 52, which correspond to the axes 40, 41 in FIG. 5. Together these differential values give a curve 53, which consequently represents the difference between comparable values of vector products on the unstressed and stressed heart. These values are here given a negative sign and are plotted from a zero line 54. They are thus obtained from the values of the curve 44, the values of curve 43 being counted at corresponding times.

In practice the inventive process is performed as follows. Electrodes are fitted to the human or animal where the measured values are to be obtained, e.g. in the manner described in U.S. Pat. No. 4,569,357. Thus, potential differences as shown in FIGS. 2 and 6 are continuously determined and supplied to a computer, which is not described in further detail here, but can correspond to that described in the aforementioned U.S. patent. The computer contains e.g. a per se known clock generator, which is used to set a clock frequency, i.e. predetermines a sequence of times. Thus, the potentials are measured (quantified) by the computer at these predetermined times and made periodically available for further processing. Such measured values determined over a longer period are preferably supplied to a memory, so that they are available there for other different processing stages. The QRS complexes, T complexes and p complexes are determined from these measured values and for this purpose their starting and final points must be found. They are preferably found according to a process described in U.S. Pat. Nos. 4,700,712 or 4,587,976. Thus, the signal or the measured values are subdivided into several periods, whose measured values can only be compared with one another. It is also possible to predetermine limit or threshold values, which classify the said measured values. Thus, e.g. all the QRS complexes can be classified according to the criteria as described for FIG. 6. From the thus classified measured values it is possible to determine all the complexes of the same class in such a way that an averaged complex is obtained for this class. For example, the QRS complex of FIG. 2 could be such an averaged QRS complex. This can also apply with regards to the loops 1 (FIG. 1), 10 (FIG. 3) and 32 (FIG. 4), which merely represent such QRS complexes in different ways.

As is also known from the aforementioned U.S. Pat. No. 4,569,357, vectors are calculated from the different values measured at each time of the sequence and then, in accordance with the aforementioned formulas, the vector products are determined from the vectors. From the said vector products and using either the known vectorial addition or simply by adding the absolute values, it is possible to calculate the sum of the vector products over entire periods for which several vector products were determined. Such periods are e.g. the averaged QRS complexes, T complexes and P complexes. This can also take place for the depolarization and repolarization periods. The depolarization periods begins with the O-point before a QRS complex and ends at the so-called I-point after the QRS complex. The repolarization period begins at the I-point and ends at the end of the T complex. As stated hereinbefore, all these points are also already determined if the starting and final points of the P, T and QRS complexes are found.

Subsequent graphic representation of the centroid vectors or vector products determined during these periods over a time axis according to FIGS. 5 and 7 then makes it possible to make comparisons between such measurements on different humans or on the same human after different times or under different stresses. Corresponding findings can be obtained if the loop 55 of the vector products 30 is determined and compared at different times and for different stresses.

What is claimed is:

1. A process for determining heart operations from acquired measured values on a living body comprising detecting electrical potentials from the body over a sequence of times of the heart cycle, deriving a plurality of vectors therefrom, selecting first and second vectors therefrom, obtaining the vector products of said first and second vectors, and determining from said vector products the heart operations.

2. A process according to claim 1 further comprising the step of determining from said plurality of vectors at the starting points and final points of the said heart cycle.

3. A process according to claim 2 further comprising the step of adding the said obtained vector products representing the said heart cycle.

4. A process according to claim 1 further comprising the step of determining the spatial pattern of the said vector products.

5. A process according to claim 4 wherein the pattern of vector products is determined in a period under stressed and unstressed conditions.

6. A process according to claim 5 wherein the pattern for the stressed and unstressed conditions is represented graphically in juxtaposed form.

* * * * *